United States Patent
Van Gelder et al.

(10) Patent No.: US 6,921,581 B2
(45) Date of Patent: Jul. 26, 2005

(54) PLASTIC FILMS CONTAINING A FRAGRANCE AND AN ODOR BARRIER MATERIAL WITHIN AND A METHOD FOR THEIR PRODUCTION

(75) Inventors: David Van Gelder, Netanya (IL); Sharon Voss, Jerusalem (IL)

(73) Assignee: Sakit Ltd., Jerusalem (IL)

( * ) Notice: Subject to any disclaimer, the term of this patent is extended or adjusted under 35 U.S.C. 154(b) by 0 days.

(21) Appl. No.: 10/445,018

(22) Filed: May 27, 2003

(65) Prior Publication Data

US 2003/0204001 A1 Oct. 30, 2003

Related U.S. Application Data

(63) Continuation-in-part of application No. PCT/IL01/01065, filed on Nov. 20, 2001.

(30) Foreign Application Priority Data

Nov. 26, 2000  (IL) .................................................. 139910

(51) Int. Cl.$^7$ ............................ B32B 27/32; C08K 5/20
(52) U.S. Cl. ........................ 428/523; 428/500; 524/232; 524/318; 524/322; 524/394; 264/176.1; 264/211
(58) Field of Search ................................ 524/232, 318, 524/322, 394; 428/500, 523; 264/176.1, 211

(56) References Cited

U.S. PATENT DOCUMENTS

| 5,496,865 | A | | 3/1996 | Heese et al. .................. 521/79 |
| H2104 | H | * | 5/2004 | Ramesh .................... 428/304.4 |

FOREIGN PATENT DOCUMENTS

| GB | 1538085 | 1/1979 |
| GB | 2194791 | 3/1988 |
| WO | WO 98/30621 | 7/1998 |

* cited by examiner

*Primary Examiner*—Peter D. Mulcahy
(74) *Attorney, Agent, or Firm*—Nixon & Vanderhye, P.C.

(57) ABSTRACT

A plastic film comprised of a polymer material, fragrance, and a waxy chemical composition for imparting to the film substantial impermeability to odors. A method for producing such films including the steps of: adding a liquid fragrance to highly porous polymer pellets; adding a waxy chemical composition to the fragrance and polymer; blending the polymer, fragrance, and waxy composition mixture; adding additional polymer to the blended mixture; extruding the resultant composition, thereby forming pellets; mixing the pellets with additional polymer; and forming a film therefrom. A plastic film, produced according to this method, for packaging or for masking unpleasant odors, comprising polyethylene or polypropylene, a fragrance, and a bis fatty-acid amide is also disclosed.

32 Claims, No Drawings

PLASTIC FILMS CONTAINING A FRAGRANCE AND AN ODOR BARRIER MATERIAL WITHIN AND A METHOD FOR THEIR PRODUCTION

CROSS-REFERENCE TO RELATED APPLICATIONS

This application is a continuation-in-part of PCT application Ser. No. PCT/IL01/01065, filed Nov. 20, 2001, which claims priority from Israel application number 139910, filed Nov. 26, 2000.

FIELD OF THE INVENTION

The present invention generally relates to plastic films containing a fragrance within the plastic material, and additionally containing a chemical composition which makes the plastic material substantially impermeable to odors. The plastic films disclosed in the present invention are useful for masking unpleasant odors such as those emitted from waste products, for example from diapers destined for disposal or from household garbage. The films according to the present invention may also be useful for packaging any other item in order to enhance its presentation or appearance by adding a pleasant fragrance, such as cosmetic items.

BACKGROUND OF THE INVENTION

Used disposable diapers tend to emit an unpleasant smell, as does household garbage. Most household garbage pails, or diaper pails, are not of a sophisticated nature, and so, when they are opened to add additional waste to them, the unpleasant odor of their contents is emitted.

The need exists, therefore, for a plastic bag that masks unpleasant odors, such as those emitted by dirty disposable diapers or household garbage. A garbage bag is known in the art that contains a fragrance, but the fragrance is sprayed on the bag externally at the end of the production process, thus the fragrance has an extremely short shelf-life, and so has limited success in masking odors once it reaches the consumer.

It is the object of the present invention to provide a plastic film that contains a fragrance incorporated within, which is released slowly over a long period of time, and has a long shelf-life. The film is impermeable to liquids, and the fragrance will mask unpleasant odors of items wrapped in the film. The film additionally contains a chemical composition which makes the plastic material substantially impermeable to odors, thereby acting as an "odor barrier". The film may be formed into a bag useful in waste disposal, or may be used in packaging of any product for which a pleasant fragrance would enhance its presentation or appearance.

It is also the object of the present invention to provide a method for producing a polyethylene or a polypropylene film having a fragrance and an odor barrier material, incorporated within.

SUMMARY OF THE INVENTION

As mentioned above, there is provided according to the present invention, a plastic film that includes a polymer material, a fragrance for masking odors and a chemical composition that acts as an odor barrier making the plastic film substantially impermeable to odors. Therefore, the film uses a dual strategy of odor containment and camouflage. The odor barrier also prevents the fragrance from dissipating rapidly, thereby extending the shelf-life of the film and articles employing such a film.

Additionally, there is provided in accordance with another aspect of the present invention, a method for producing a film for packaging and for masking odors. The method includes the steps of a) providing a liquid fragrance to highly porous pellets of a polymer;

b) blending the mixture with a chemical composition that makes the polymer substantially impermeable to odors;

c) diluting the blended mixture with a powdered polymer;

d) forming pellets from the diluted blended mixture;

e) adding a polymer to the formed pellets and blending the polymer and pellets together; and f) producing a film from the blend.

There is provided in accordance with yet another aspect of the present invention, a method for producing a polyethylene or polypropylene film having a fragrance and an odor barrier material incorporated into the film, comprising the steps of adding a liquid fragrance to highly porous pellets of polyethylene or polypropylene polymer or co-polymers thereof at a weight ratio of polymer to fragrance of 3:1 and mixing the combination at 30–40 RPM for approximately five to ten minutes. Then, powdered bis fatty-acid amide is added to the above, at a weight ratio of 3–25%, and further mixing is carried out for an additional five minutes. Polyethylene or polypropylene polymer or co-polymer of approximate particle size of $500\mu$ is added to the mixture at a ratio of 1:1 by weight, the composition is mixed for two minutes at 60 RPM, and extruded on a single screw extruder. The mixture is formed into pellets, which are mixed with polyethylene or polypropylene polymer or co-polymers thereof at a ratio of 100:1 to 20:1 of polymer to above composition. A film is formed.

Further in accordance with one preferred embodiment the powdered bis fatty-acid amide is the product of a diamine and a monocarboxylic acid, the acid being selected from the group consisting of lauric acid, myristic acid, palmitic acid, stearic acid, 12-hydroxy-stearic acid, arachidic acid, and behenic acid. Such bis fatty-acid amides are known per se.

Moreover, in accordance with one preferred embodiment the powdered bis fatty-acid amide is present at a ratio of 3–25% by weight.

Still further in accordance with one preferred embodiment the fragrance incorporated within the film is of any source, including a natural or artificial fragrance.

The present invention also relates to a plastic film having a fragrance included in the film, the film produced according to the above-mentioned method and used for either packaging or for masking unpleasant odors. The plastic film is made from a polyethylene or polypropylene polymer or co-polymers thereof and from a bis fatty-acid amide, which acts as an odor barrier.

In accordance with one preferred embodiment, the plastic film is formed into a bag useful for packaging or for masking unpleasant odors.

Additionally in accordance with one preferred embodiment, the polyethylene or polypropylene polymer, or co-polymers thereof in the film is supplied in pellet form.

Additionally in accordance with one preferred embodiment the fragrance incorporated within the film is a combination of more than one fragrance.

Furthermore, in accordance with one preferred embodiment the fragrance incorporated within the bag has the smell of talcum powder.

DETAILED DESCRIPTION OF THE PREFERRED EMBODIMENTS

The present invention provides a plastic film that includes a plastic material, a fragrance for masking odors and a chemical composition that acts as an odor barrier by making the plastic film substantially impermeable to odors. The odor barrier also prevents the fragrance from dissipating rapidly, thereby extending the shelf-life of such films and articles employing such films. The invention also provides a method for producing such films, the method using a fragrance impregnated polymer pellet, which additionally is loaded with a chemical composition imparting substantial odor impenetrability to the film. Typical end-uses of such films are garbage bags, diapers, food packaging, and the like.

The polymers used in films of the present invention typically are polyethylene, polypropylene and copolymers thereof, but other polymers may also be used. Without being limiting, these may include ethylene vinyl acetate (EVA), ethylene butyl acetate (EBA), and ethylene ethyl acetate (EEA).

The odor barrier chemical composition is typically a waxy composition. Typically, and without being limiting, the waxy composition is a bis fatty-acid amide or montanic acid, its esters and soaps.

The bis fatty-acid amides which are used are generally applied in powdered form and are the products of a diamine and a monocarboxylic acid, the acid being selected from any of the following fatty acids: lauric acid, myristic acid, palmitic acid, stearic acid, 12-hydroxy-stearic acid, arachidic acid, and behenic acid. Such bis fatty-acid amides are known per se. The preceding list should be thought of as being exemplary only and non-limiting. Particularly preferred is the bis amide of behenic acid.

Bis amides are known in the art and commercially available from suppliers such as Croda Chemicals Europe Ltd (UK) and Akzo.

The waxy composition is present in a ratio of about 3% to about 25%, preferably 3% to 15% of the initial amide-fragrance-polymer mixture, before diluting the mixture further with additional polymer. The percentage of his fatty-acid amide in the film produced is about 0.015% to about 0.62%, preferably between about 0.15% and about 0.5%.

The fragrances used can consist of a single fragrance or multiple fragrances, as desired. Similarly, the fragrances may be natural or artificial fragrances. Without being limiting, fragrances typically constitute about 0.1 to about 0.6% of the film. The fragrance concentration is generally determined by the end use of the product. Fragrances used in this invention are readily available commercially.

It would not be obvious to try a combination of fragrances and waxy compositions because, in general, waxes have a tendency to migrate quickly to the surface of polyolefin films. It would be expected that volatile fragrances would move to the film's surface together with the waxes, thereby shortening the shelf-life of the scented film.

Surprisingly, however, waxy compositions based on amides of fatty acids behave differently from other waxy compositions comprised of low molecular weight polyethylene and synthetic Fischer-Tropsch waxes. Waxy compositions constituting amides of fatty acids have been found to prevent volatile fragrances from rapid migration to the surface of a film.

The method for producing the films discussed above includes the steps of: providing a liquid fragrance to highly porous pellets of a polymer; blending the mixture with a chemical composition that makes the polymer substantially impermeable to odors; diluting the blended mixture with a powdered polymer; forming pellets from the diluted blended mixture; adding a polymer to the formed pellets in a w/w ratio of 20:1 to 100:1 of the total mixture and blending the polymer and pellets together; and producing a film from the blend.

Typically, the polymers used in the method are polyethylene, polypropylene and copolymers thereof, but other polymers may also be used. Without being limiting, these may include ethylene vinyl acetate (EVA), ethylene butyl acetate (EBA), and ethylene ethyl acetate (EEA).

The odor barrier chemical composition used in the method is typically waxy composition. Typically, and without being limiting, the waxy composition is a bis fatty-acid amide or montanic acid, its esters and soaps.

Bis fatty-acid amides are generally applied in powdered form and are the product of a diamine and a monocarboxylic acid, the acid being chosen from among the following fatty acids: lauric acid, myristic acid, palmitic acid, stearic acid, 12-hydroxy-stearic acid, arachidic acid, and behenic acid. The preceding list should be deemed to be exemplary only and non-limiting. Particularly preferred are bis amides of behennic acid.

The waxy composition is present in a ratio of about 3% to about 25%, preferably from about 3% to about 15% of the initial amide-fragrance-polymer mixture, before diluting the mixture further with additional polymer. The percentage of bis fatty-acid amide in the film produced is about 0.015% to about 0.62%, preferably between about 0.15% and about 0.5%.

The fragrances used can consist of a single fragrance or multiple fragrances, as desired. Similarly, the fragrances may be natural or artificial fragrances. Without being limiting, fragrances typically constitute about 0.1 to about 0.6% of the film. The fragrance concentration is generally determined by the end use of the product. Fragrances used in this invention are readily available commercially.

In the present invention, a fragrant film can be produced using either polyethylene or polypropylene. A highly porous polymer or co-polymer in pellet form is used, having a void volume of 30–80% and a bulk density of 350 kg/m$^3$. The polymer is mixed in a Henschel-type mixer with a liquid fragrance at a weight ratio of polymer to fragrance of 3:1. Mixing is carried out at 30–40 RPM for five to ten minutes, at 20–25° C. (room temperature). Fragrance is absorbed in the porous polymer by capillary force. Fragrance used emitted the smell of talcum powder.

A powdered bis fatty-acid amide is then added at a ratio of 3–25% by weight to the above composition, and mixed for an additional five minutes. The waxy nature of the bis fatty-acid amide prevents premature evaporation of the fragrance during processing and prolongs the shelf-life of the fragrance in the end product to at least six months. The bis fatty-acid amide also acts as an odor barrier, preventing the escape of foul odor of the waste material to be stored inside the film. The powdered bis fatty-acid amide is the product of a diamine and a monocarboxylic acid, the acid being selected from one of the following: lauric acid, myristic acid, palmitic acid, stearic acid, 12-hydroxy-stearic acid, arachidic acid, and behenic acid. Such bis fatty amides are known per se. Alternatively, montanic acid and its esters and soaps can also be used as the odor barrier. Polymer with an approximate particle size of 500$\mu$ is then added at a ratio of 1:1 with the above mixture. The entire composition is mixed for an additional two minutes at 60 RPM, then extruded on a single-screw extruder and formed into pellets. The product is then referred to as a "master batch" which can be used to produce polyethylene or polypropylene films, to be applied for use as, for example, a fragrant plastic bag used for masking unpleasant odors. The ratio of polyethylene or polypropylene to "master batch" is between 100:1 to 20:1.

While in the above a single-screw extruder has been used, it is evident to one skilled in the art that other types of extruders such as double-screw and blow extruders can be used as can other film producing methods such as cast extrusion.

It should be evident to one skilled in the art that the method described herein recites a method for producing a master batch fragrant carrier polymer which can be used for forming plastic films.

It will be appreciated by persons skilled in the art that the present invention is not limited by what has been particularly shown and described herein above. Rather the scope of the invention is defined by the claims that follow.

What is claimed is:

1. A film for packaging a product or for masking unpleasant odors, comprising:
    a polyolefin;
    a compound which makes said film substantially impermeable to odors, said compound selected from a group of compounds consisting of bis fatty acid amides, montanic acid, esters of montanic acid and soaps of montanic acid; and
    a fragrance for masking odors.

2. A film according to claim 1 wherein said polyolefin is selected from a group consisting of polyethylene, polypropylene and co-polymers thereof.

3. A film according to claim 1, wherein said bis fatty acid-amide is the product of a diamine and a monocarboxylic acid, said acid being selected from a group consisting of lauric acid, myristic acid, palmitic acid, stearic acid, 12-hydroxy-stearic acid, arachidic acid, and behenic acid.

4. A film according to claim 3, wherein said bis fatty-acid amide is a bis fatty-acid amide of behenic acid.

5. A bag made from a film, said film comprised as in claim 1.

6. A packaging material made from a film, said film comprised as in claim 1.

7. A method for producing an odor masking film for packaging, said method comprising the steps of:
    a) providing a liquid fragrance to highly porous pellets of a polyolefin;
    b) blending the polyolefin-fragrance mixture with a compound that makes the film substantially impermeable to odors, the compound being selected from a group of compounds consisting of bis fatty acid amides, montanic acid, esters of montanic acid and soars of montanic acid;
    c) diluting the blended mixture with a powdered polyolefin;
    d) forming pellets from the diluted blended mixture;
    e) adding a polyolefin to the formed pellets and blending the polymer and pellets together; and
    f) producing a film from the blend.

8. A method according to claim 7 wherein said step of producing is an extrusion step.

9. A method according to claim 7 further including a step of mixing, after said step of providing and prior to said step of blending, in which the fragrance is mixed with the porous pellets.

10. A method according to claim 7, wherein in said steps of providing, diluting and adding, the polyolefin is selected from a group of polyolefins consisting of polyethylene, polypropylene and co-polymers of polyethylene or polypropylene.

11. A method according to claim 7, wherein the bis fatty-acid amide is the product of a diamine and a monocarboxylic acid, the acid being selected from a group consisting of lauric acid, myristic acid, palmitic acid, stearic acid, 12-hydroxy-stearic acid, arachidic acid, and behenic acid.

12. A method according to claim 7, wherein in said step of blending the bis fatty-acid amide comprises about 3% to about 25% by weight of the total mixture, where the mixture contains the bis amide, the fragrance and the polymer.

13. A method according to claim 7, wherein in said step of adding, the polymer is added in a w/w ratio of 20:1 to 100:1 of the formed pellets.

14. A film produced according to the method defined in claim 7, said film including:
    polyethylene or polypropylene;
    a bis fatty-acid amide; and
    a fragrance,
    wherein said polyethylene or polypropylene and said bis fatty-acid amide act as an odor barrier.

15. A method for producing a polyethylene or polypropylene film having a fragrance and an odor barrier material incorporated into said film, said method comprising the steps of:
    a) adding a liquid fragrance to highly porous pellets of polyethylene or polypropylene polymer or co-polymers thereof at a weight ratio of polymer to fragrance of 3:1, which yields a mixture;
    b) blending said mixture at 30–40 RPM for approximately five to ten minutes;
    c) adding a powdered bis fatty-acid amide at a weight ratio of 3–25%, to the mixture;
    d) blending the mixture for an additional five minutes;
    e) adding polyethylene or polypropylene polymer or co-polymers thereof, of approximate particle size of 500$\mu$ at a ratio of 1:1 by weight to the mixture;
    f) blending the mixture for two minutes at 60 RPM to yield a resultant composition; g) extruding the resultant composition on a screw extruder;
    h) forming the composition into pellets;
    i) mixing said pellets with polyethylene or polypropylene polymer or co-polymers thereof at a w/w ratio of 100:1 to 20:1 of polymer to the composition; and
    j) forming a film from said pellets.

16. A method according to claim 15, wherein the powdered bis fatty-acid amide is the product of a diamine and a monocarboxylic acid, the acid being selected from the group consisting of lauric acid, myristic acid, palmitic acid, stearic acid, 12-hydroxy-stearic acid, arachidic acid, and behenic acid.

17. A method according to claim 15, wherein the fragrance incorporated within said film is of any source, including a natural or artificial fragrance.

18. A film produced according to the method as defined in claim 15, said film comprising:
    polyethylene or polypropylene;
    a bis fatty-acid amide; and
    a fragrance,
    wherein said polyethylene or polypropylene and said bis fatty-acid amide act as an odor barrier.

19. A bag for either packaging or for masking unpleasant odors, comprising a polyethylene or polypropylene film as defined in claim 18.

20. A film according to claim 18, wherein the polyethylene or polypropylene polymer or co-polymers thereof from which said film is formed is in pellet form.

21. A film according to claim 18, wherein the fragrance incorporated within said film is a combination of more than one fragrance.

22. A film according to claim 18, wherein the fragrance incorporated within said film has the smell of talcum powder.

23. A film according to claim 1 wherein said compound is present in a concentration of 0.02–0.6% by weight of the total film, and said fragrance for masking odors is present in a concentration of 0.1–0.6 % by weight of the total film.

24. A film according to claim 23 wherein said compound is present in a concentration of 0.04–0.5% by weight of the total film.

25. A film according to claim 23 wherein said fragrance for masking odors is present in a concentration of 0.16–0.5 % by weight of the total film.

26. A film according to claim 23 wherein said compound is present in a concentration of 0.04–0.5% by weight of the total film and wherein said fragrance for masking odors is present in a concentration of 0.16–0.5 % by weight of the total film.

27. A method according to claim 7 wherein said fragrance is present in a concentration of 0.1–0.6 % by weight of the total film and said compound is present in a concentration of 0.02–0.6 % by weight of the total film.

28. A method according to claim 27 wherein the fragrance is present in a concentration of 0.16–0.5 % by weight of the total film.

29. A method according to claim 27 wherein the compound is present in a concentration of 0.04–0.5 % by weight of the total film.

30. A method according to claim 27 wherein the fragrance is present in a concentration of 0.16–0.5 % by weight of the total film and wherein the compound is present in a concentration of 0.04–0.5 % by weight of the total film.

31. A method according to claim 7 further including a step of selecting a compound, the compound being selected from a group of compounds consisting of bis fatty acid amides, montanic acid, esters of montanic acid and soaps of montanic acid said step of selecting being effected prior to said step of blending.

32. A method according to claim 10 further including a step of selecting in said steps of providing, diluting and adding wherein the polyolefin is selected from a group of polyolefins consisting of polyethylene, polypropylene and co-polymers of polyethylene or polypropylene.

\* \* \* \* \*